United States Patent [19]

Chung et al.

[11] Patent Number: 5,231,209
[45] Date of Patent: Jul. 27, 1993

[54] METHOD OF INHIBITING LUNG TUMORS, ARYLALKYL ISOTHIOCYANATES, AND METHOD OF SYNTHESIZING SAME

[75] Inventors: Fung-Lung Chung, Yorktown Heights; Stephen S. Hecht, Larchmont, both of N.Y.; Karin Eklind, Riverside, Conn.; Mark A. Morse, Croton-on-Hudson, N.Y.

[73] Assignee: American Health Foundation, New York, N.Y.

[21] Appl. No.: 806,668

[22] Filed: Dec. 13, 1991

Related U.S. Application Data

[60] Division of Ser. No. 531,023, May 31, 1990, Pat. No. 5,114,969, which is a continuation-in-part of Ser. No. 326,964, Mar. 22, 1989, abandoned.

[51] Int. Cl.$^5$ .................... C07C 331/00; C07C 13/00
[52] U.S. Cl. ........................................ 558/17; 585/24
[58] Field of Search ............................ 558/17; 585/24

[56] References Cited

PUBLICATIONS

VanEtten et al, "Glucosinolates and Derived Products in Cruciferous Vegetables" J. Agric. Food Chem. vol. 24, No. 3, 1976, pp. 452-455.

Wattenberg, "Inhibition of Carcinogenic Effects of Polycyclic Hydrocarbons by Benzyl Isothiocyanates and Related Compounds" J. Natl. Can. Inst. vol. 56, No. 2, Feb. 1977, pp. 395-398.

Wattenberg, "Inhibition of Carcinogen-induced Neoplasia by Sodium Cyanate, tert-Butyl Isocyanate, and Benzyl Isothiiocyanate" Can. Res. 41, 2991-2994, Aug. 1981.

Fung-Lung Chung, Minyao Wang, and Stephen S. Hecht: "Effects of Dietary Indoles and Isothiocyanates on N-Nitrosodimethylamine and 4-(Methylnitrosamino-1-(3-Pyridyl)1-Butanone α-Hydroxylation and DNA Methylation in Rat Liver"; Carcinogenesis; vol. 6, No. 4, pp. 539-543, 1985.

Wattenberg "Inhibitory effects of benzyl isothiocya-nates..." Carcinogenesis vol. 8, No. 12, pp. 1971-1973, 1987.

Morse et al "Inhibition of 4-(Methylnitrosamino)-1-(-3-pyridyl)-1-butanone–induced DNA Adduct Formation and Tumorigenicity in the Lung of F344 Rats by Dietary Phenethyl Isothiocyanate" Cancer Research 49, 549-553, Feb. 1, 1989.

Chung et al, Chemical Abstracts vol. 102:214760w.

Effects of Aromatic Isothiocyanates on Tumorigenicity, $O^6$-Methylguanine Formation, and Metabolism of the Tabacco-specific Nitrosamine 4-(Methylnitrosamino)-1-Cancer Research 49, 2894-2897, Jun. 1, 1989.

Effects of alkyl chain length on the inhibition of NNK-induced lung neoplasia in A/J mice by arylalkyl isothiocyanates Carcinogenesis vol. 10, No. 9, pp. 1757-1759, 1989.

Morse et al, *Structure-Acitivity Relationships For Inhibition of 4-(Methylnitrosamino)-1-(3-pyridyl)-1-butanone Lung Tumorigenesis by Arylalkyl Isothiocyanates in A/J Mice*, Apr. 1, 1991, Cancer Research 51, pp. 1846-1850.

*Primary Examiner*—Nathan M. Nutter
*Attorney, Agent, or Firm*—Ladas & Parry

[57] ABSTRACT

A method of inhibiting lung tumor multiplicity and/or incidence by treating mammals with relatively long chain arylalkyl isothiocyanates, especially effective with respect to tumors induced by exposure to tobacco-specific nitrosamine. Among the isothiocyanates are 4-phenylbutyl isothiocyanate, phenylpentyl isothiocyanate and phenylhexyl isothiocyanate, which are synthesized by adding hydrochloride of phenylbutylamine, phenylpentylamine, or phenylhexylamine in water to thiophosgene in an inert organic solvent. For comparison testing, oxo-pyridyl butyl isothiocyanate is synthesized by dissolving myosmine in HCl to obtain a hydrochloride salt, suspending the salt in dry chloroform, adding thiophosgene, and adding chloroform containing triethylamine.

1 Claim, No Drawings

METHOD OF INHIBITING LUNG TUMORS, ARYLALKYL ISOTHIOCYANATES, AND METHOD OF SYNTHESIZING SAME

This is a divisional of copending application Ser. No. 07/531,023 filed on May 31, 1990 and now U.S. Pat. No. 5,114,969 which is a continuation-in-part of Ser. No. 07/326,964 of Mar. 22, 1989 and now abandoned.

BACKGROUND

In other studies which we have made, we have considered the effects of glucosinolates. Glucosinolates are naturally-occurring constituents of cruciferous vegetables (Tookey, H. L., VanEtten, C. H. and Daxenbichler, M. E. (1980) Glucosinolates. In Liener, I. E. (ed.), *Toxic Constituents of Plant Foodstuffs.* Second Edition, Academic Press, New York, Chapter 4, pp. 103–142). Sinigrin and glucobrassicin are two major glucosinolates found in cabbage, cauliflower, and brussels sprouts (Sones, K., Heaney, R. K. and Fenwick, G. R. (1984) An estimate of the mean daily intake of glucosinolates from cruciferous vegetables in the UK. *J. Sci. Food Agric.,* 35, 712–720; VanEtten, C. H., Daxenbichler, M. E., Williams, P. H. and Kwolek, W. F. (1976) Glucosinolates and derived products in cruciferous vegetables. Analysis of the edible part from twenty-two varieties of cabbage. *J. Agric. Food Chem.,* 24, 452–455). Indole-3-carbinol (I3C) is a major product of thioglucosidase-catalyzed hydrolysis of glucobrassicin (Loub, W. D., Wattenberg, L. W. and Davis, D. W. (1975) Aryl hydrocarbon hydroxylase induction in rat tissues by naturally occurring indoles of cruciferous plants. *J. Natl. Cancer Inst.,* 54, 985–988; Bradfield, C. A. and Bjeldanes, L. F. (1987) High-performance liquid chromatographic analysis of anticarcinogenic indoles in *Brassica oleracea. J. Agric. Food Chem.,* 35, 46–49). Glucosinolates and their derived isothiocyanates and indoles can modulate tumorigenesis. Glucobrassicin and glucotropaeolin, the precursor of benzyl isothiocyanate, decreased tumors induced by benzo[a]pyrene (BP) in ICR/Ha mouse lung, BP-induced pulmonary adenomas in A/J mice, and mammary tumors induced by 7,12-dimethylbenz[a]anthracene (DMBA) in Sprague-Dawley rats when each glucosinolate was administered orally prior to carcinogen dosing (Wattenberg, L. W., Hanley, A. B., Barany, G., Sparnins, V. L., Lam, L. K. T. and Fenwick, G. R. (1986) Inhibition of carcinogenesis by some minor dietary constituents. In Hayashi, Y., Nagao, M., Sugimura, T., Takayama, S., Tomatis, L., Wattenberg, L. W. and Wogan, G. N. (eds), *Diet Nutrition and Cancer.* Japan Sci. Soc. Press, London/VNU Sci. Press, Utrecht, pp. 193–203). I3C, a good inducer of aryl hydrocarbon hydroxylase and glutathione-S-transferase (Loub, W. D., Wattenberg, L. W. and Davis, D. W. (1975) Aryl hydrocarbon hydroxylase induction in rat tissues by naturally occurring indoles of cruciferous plants. *J. Natl. Cancer Inst.,* 54, 985–988; Wattenberg, L. W., Loub, W. D., Lam, L. K. and Speier, J. L. (1976) Dietary constituents altering the responses to chemical carcinogens. *Fed. Proc.,* 35, 1327–1331; Sparnins, V. L., Venegas, P. L. and Wattenberg, L. W. (1982) Glutathione-S-transferase activity: enhancement by compounds inhibiting chemical carcinogenesis and by dietary constituents. *J. Natl. Cancer Inst.,* 68, 493–496), has been found to inhibit BP-induced neoplasia in ICR/Ha forestomach, DMBA-induced mammary neoplasia in Sprague-Dawley rats and aflatoxin $B_1$-induced hepatic tumorigenicity in rainbow trout when administered by gavage or in the diet (Wattenberg, L. W.., and Loub, W. D. (1978) Inhibition of polycyclic aromatic hydrocarbon-induced neoplasia by naturally occurring indoles. *Cancer Res.,* 38, 1410–1413; Nixon, J. E., Hendricks, J. D., Pawlowski, N. E., Pereira, C. B., Sinnhuber, R. O. and Bailey, G. S. (1984) Inhibition of aflatoxin $B_1$ carcinogenesis in rainbow trout by flavone and indole compounds. *Carcinogenesis,* 5, 615–619).

The tobacco-specific nitrosamine, 4-(methylnitrosamino)-1-(3-pyridyl)-1-butanone (NNK), is the most potent carcinogenic nitrosamine found in tobacco (Hecht, S. S., Trushin, N., Castonguay, A. and Rivenson, A. (1986) Comparative tumorigenicity and DNA methylation in F344 rats by 4-(methylnitrosamino)-1-(3-pyridyl)-1-butanone and N-nitrosodimethylamine. *Cancer Res.,* 46, 498–502). The ability of NNK to induce a high incidence of lung tumors at low doses regardless of the route of administration in all animal species tested (Hecht, S. S., Trushin, N., Castonguay, A. and Rivenson, A. (1986) Comparative tumorigenicity and DNA methylation in F344 rats by 4-(methylnitrosamino)-1-(3-pyridyl)-1-butanone and N-nitrosodimethylamine. *Cancer Res.,* 46, 498–502; International Agency for Research on Cancer (1985) Evaluation of the carcinogenic risk of chemicals to humans: tobacco habits other than smoking; Betel-Quid and Areca-nut chewing; and some related nitrosamines. *IARC Monographs,* 37, 209–224) suggests a possible role in the induction of lung cancer in smokers. When administered s.c. in rats, NNK also induces tumors of the liver and nasal cavity. While sinigrin inhibited NNK metabolism and its subsequent DNA methylation in liver, I3C enhanced hepatic metabolism of NNK (Chung, F.-L., Wang, M. and Hecht, S. S. (1985) Effects of dietary indoles and isothiocyanates on N-nitrosodimethylamine and 4-(methylnitrosamino)-1-(3-pyridyl)-1-butanone alpha-hydroxylation and DNA methylation in rat liver. *Carcinogenesis,* 6, 539–543). We have also examined in three NNK target tissues the effects of dietary sinigrin and I3C on two factors which may be important in NNK tumorigenesis: DNA methylation and $O^6$-methylguanine-DNA transmethylase activity. The results of these studies were compared with tumorigenicity data obtained from a two-year bioassay in which NNK-treated rats were fed control or sinigrin-containing diets.

We previously demonstrated that isothiocyanates, such as phenethyl isothiocyanate and phenyl isothiocyanate showed a wide range of inhibitory activities toward demethylation of nitrosamines, including NNK, in acute and chronic studies. Chronic, but not acute, pretreatment with sinigrin also caused a significant decrease in the demethylation of NDMA and NNK. The effects of phenethyl isothiocyanate, phenyl isothiocyanate, and sinigrin on the in vivo methylation of DNA by NDMA and NNK were also evaluated. (Chung, Fung-Lung; Wang, Minyao; Hecht, Stephen S. *Chemical Abstracts* 102:214760W(1985)). The results were parallel to those obtained in the in vitro assays. Phenethyl isothiocyanate, phenyl isothiocyanate, and sinigrin generally inhibited the formation of 7-methylguanine and $O^6$-methylguanine in rat hepatic DNA. The results of that study suggested that these compounds could be tested to determine if they were anticarcinogenic to NNK. The results did not suggest the remarkable inhibitory effects which we have now discovered are possessed by the compounds of the instant invention.

SUMMARY OF INVENTION

It is an object of the invention to provide a method of inhibiting lung tumor multiplicity and/or incidence.

It is another object of the invention to develop arylalkyl isothiocyanates for use in the treatment of mammals.

It is still another object of the invention to provide new methods for the synthesizing of isothiocyanates.

In achieving the above and other objects of the invention, there is provided a method which comprises inhibiting lung tumor multiplicity and/or incidence by treating mammals with relatively long chain arylalkyl isothiocyanates. These isothiocyanates may be selected from the group consisting of phenethyl, phenylpropyl, phenylbutyl, phenylpentyl and phenylhexyl isothiocyanates. These isothiocyanates may be administered to inhibit lung tumors induced by tobacco-specific nitrosamine and, more particularly, 4-(methylnitrosamino)-1-(3-pyridyl)-1-butanone.

4-Phenylbutyl isothiocyanate, phenylpentyl isothiocyanate and phenylhexyl isothiocyanate have been in accordance with the invention synthesized for the first time. This is generally accomplished by adding hydrochloride of phenylbutylamine, phenylpentylamine, or phenylhexylamine in water to thiophosgene in an inert organic solvent, adding a base solution to the thusly obtained aqueous phase, and recovering the phenylalkyl isothiocyanate therefrom.

Also provided in accordance with the invention is a further form of isothiocyanate for comparison testing purposes. This further isothiocyanate is oxo-pyridyl butyl isothiocyanate, which has also been synthesized in accordance with the invention for the first time. The method of synthesizing comprises in accordance with the invention a method whereby myosmine is dissolved in hydrochloric acid to obtain a hydrochloride salt, and then suspending the salt in dry chloroform, adding thiophosgene, adding chloroform containing triethylamine, and recovering oxo-pyridyl butyl isothiocyanate.

Other objects, features, and advantages of the invention will be found in the detailed description, which follows hereinbelow.

DETAILED DESCRIPTION

Six arylalkyl isothiocyanates were initially evaluated for their abilities to inhibit pulmonary adenomas induced by the tobacco-specific nitrosamine 4-(methylnitrosamino)-1-(3-pyridyl)-1-butanone (NNK) in A/J mice. As will be discussed hereinafter, phenyl isothiocyanate (PITC), benzyl isothiocyanate (BITC), phenethyl isothiocyanate (PEITC), 3-phenylpropyl isothiocyanate (PPITC), 4-phenylbutyl isothiocyanate (PBITC), 4-oxo-4-(3-pyridyl)butyl isothiocyanate (OPBITC), and corn oil were administered to mice daily by gavage (5 $\mu$mol/mouse) for four(4) consecutive days. At 2 hours following the final dosing, mice were administered saline or 10 $\mu$mol of 4-(methylnitrosamino)-1-(3-pyridyl)-1-butanone (NNK) i.p. Pulmonary adenomas were quantitated at 16 weeks after NNK administration. 100% of mice administered only corn oil prior to NNK developed tumors, with an average multiplicity of 9.2 tumors/mouse. Pretreatment with PITC, BITC, and OPBITC had no significant effects on NNK-induced lung neoplasia. However, PEITC pretreatment resulted in a 64% reduction of lung tumor multiplicity, but did not affect the percentage of mice that developed tumors. Both PPITC and PBITC decreased tumor multiplicity by 96% and the percentage of tumor-bearing animals by more than 60%. These results demonstrated increasing inhibition of NNK-induced lung neoplasia by arylalkyl isothiocyanates with increasing alkyl chain length. Also demonstrated were the inhibitory effects of PPITC and PBITC, two isothiocyanates that previously had never been tested as chemopreventive agents. Also shown was the inhibitory effect of PEITC, although at increased dosage.

Among the tobacco-specific nitrosamines, 4-(methylnitrosamino)-1-(3-pyridyl)-1-butanone (NNK) is the most potent carcinogen known (Hoffmann, D. and Hecht, S. S. (1985), Nicotine-derived N-nitrosamines and tobacco-related cancer: current status and future directions, Cancer Res., 45, 935-944). NNK has been shown to induce lung tumors in all animal species tested by a variety of routes of administration (Hoffmann, D. and Hecht, S. S. (1988), Smokeless tobacco and cancer, ISI Atlas of Science: Pharmacology, 46-52; Hecht, S. S. and Hoffmann, D. (1988), Tobacco-specific nitrosamines, an important group of carcinogens in tobacco and tobacco smoke, Carcinogenesis, 9, 875-884). These findings implicate NNK in the induction of lung cancer in smokers. Thus, the development of effective chemopreventive strategies for NNK-induced tumorigenesis in animal models will be beneficial to human populations.

Isothiocyanates have been shown to be effective inhibitors of tumorigenesis in several different animal models. Phenyl isothiocyanate (PITC), benzyl isothiocyanate (BITC), and phenethyl isothiocyanate (PEITC) inhibited mammary tumor formation in Sprague-Dawley rats when administered orally prior to 7,12-dimethylbenz (a)anthracene (DMBA) (Wattenberg, L. W. (1978), Inhibition of carcinogenic effects of polycyclic hydrocarbons by benzyl isothiocyanate and related compounds, J. Natl. Cancer Inst., 58, 395-398). In the same study, dietary BITC and PEITC inhibited DMBA-induced neoplasia of the forestomach and lung of ICR/Ha mice. Dietary BITC also inhibited DMBA-induced mammary neoplasia in Sprague-Dawley rats when given subsequent to carcinogen exposure (Wattenberg, L. W. (1981), Inhibition of carcinogen-induced neoplasia by sodium cyanate, tert-butyl isocyanate, and benzyl isothiocyanate administered subsequent to carcinogen exposure, Cancer Res., 41, 2991-2994). BITC pretreatment also reduced benzo(a)pyrene-induced lung and forestomach tumors and N-nitrosodiethylamine-induced forestomach tumors in A/J mice (Wattenberg, L. W. (1987), Inhibitory effects of benzyl isothiocyanate administered shortly before diethylnitrosamine or benzo(a)pyrene on pulmonary and forestomach neoplasia in A/J mice, Carcinogenesis, 8, 1971-1973).

Recently, we have shown that PEITC inhibited lung tumorigenesis induced by NNK in F344 rats (Morse, M. A.; Wang, C-X.; Stoner, G. D.; Mandal, S.; Conran, P. B.; Amin, S. G.; Hecht, S. S.; and Chung, F-L. (1989), Inhibition of 4-(methylnitrosamino)-1-(3-pyridyl)-1-butanone (NNK)-induced DNA adduct formation and tumorigenicity in lung of F344 rats by dietary phenethyl isothiocyanate, Cancer Res., 49, 549-553). We also tested PITC, BITC, and PEITC for inhibition of NNK-induced lung neoplasia in A/J mice (Morse, M. A.; Amin, S. G.; Hecht, S. S.; and Chung, F-L. (1989), Effects of aromatic isothiocyanates on tumorigenicity, $O^6$-methylguanine formation, and metabolism of the tobacco-specific nitrosamine 4-(methylnitrosamino)-1-(3-pyridyl)-1-butanone in A/J mouse lung, Cancer Res., 49, 2894-2897 (1989)). While PEITC proved again to be a potent inhibitor of NNK-induced lung tumors, the shorter-chain arylalkyl isothiocyanate homologues PITC and BITC were ineffective. By way of further exploration into the structure-activity relationships of isothiocyanates towards inhibition of NNK-induced lung neoplasia, we tested PITC, BITC, and PEITC, as well as three longer-chain compounds that had previously not been evaluated for their inhibitory potential: 3-phenylpropyl isothiocyanate (PPITC), and a newly-synthesized isothiocyanate, 4-phenylbutyl isothiocyanate (PBITC) and 4-oxo-4-(3-pyridyl)butyl isothiocyanate (OPBITC).

NNK was synthesized as known (Hecht, S.S., Lin, D., and Castonguay, A. (1983), Effects of alpha-deuterium substitution on the mutagenicity of 4-(methylnitrosamino)-1-(3-pyridyl)-1-butanone (NNK), *Carcinogenesis*, 4, 305–310). PITC, BITC, and PEITC were obtained from Aldrich Chemical Co. (Milwaukee, WI). PPITC was obtained from Fairfield Chemical Co. (Blythewood, SC). PBITC and OPBITC were synthesized as described below.

Synthesis of PBITC: the hydrochloride of phenylbutylamine (1.85 g.) in 5 ml. of water was added to thiophosgene (1.28 g.) in 10 ml. of an inert organic solvent such as chloroform (methylene chloride may also be used) with stirring at room temperature. 10% NaOH or KOH solution was added dropwise to the mixture at a rate such that the alkaline pH of the aqueous phase was maintained. After the final addition of NaOH, the reaction mixture was stirred for an additional hour. The chloroform phase was washed with $H_2O$, dried over $MgSO_4$ or $Na_2SO_4$, and concentrated in vacuo to give crude PBITC. The crude product was purified on a silica gel column eluted with toluene to yield 1.71 g. of pure compound. $^{13}C$ NMR was performed on a 360 MHz Bruker spectrophotometer. $^{13}C$ NMR ($CDCl_3$): δ 141.4, 128.3, 125.4 (C-aromatic), 44.9 (C-1), 34.9 (C-4), 29.5 and 28.0 ppm (C-2 and C-3). MS: m/e 191 (M+). IR abs: 2060 $cm^{-1}$. Calculated for $C_{11}H_{13}NS$-C: 69.06, H: 6.85; N: 7.32; S: 16.76, Found C: 69.05, H: 6.95; N: 6.93; S: 1659.

Synthesis of OPBITC: myosmine was dissolved in 1.0 N HCl, stirred for 30 minutes, and evaporated in vacuo to dryness to yield 4-oxo-4-(3-pyridyl) butylamine hydrochloride. The hydrochloride salt was suspended in 20 ml. of dry chloroform under $N_2$ and cooled to $-30°$ C. Following addition of thiophosgene (0.38 ml.), 10 ml. of chloroform containing triethylamine (2.23 ml.) was slowly added. The reaction mixture was stirred for an additional hour at 30° C., and then allowed to reach room temperature. The chloroform solution was washed with $H_2O$, dried over $MgSO_4$. It was then concentrated in vacuo to a small volume and applied to a silica gel column eluted with 50% toluene: 50% ethyl acetate to yield pure OPBITC (0.86 g.). $^{13}C$ NMR ($CDCl_3$): δ 197.2 (C-4), 153.8, 149.5, 135.3, 131.7, 123.7 (C-pyridyl ring), 44.4 (C-1), 35.1 (C-3), 24.0 ppm (C-2). $^1H$ NMR ($CDCl_3$): δ 9.16 (d, 2-pyridyl), 8.78 (dd, 6-pyridyl), 8.22 (ddd, 4-pyridyl), 7.42 (dd, 5-pyridyl), 3.67 (t, H-1), 3.14 (t, H-3), 2.15 ppm (tt, H-2). MS: m/e 206 (M+).

Female A/J mice (Jackson Laboratories, Bar Harbor, ME) were housed in polycarbonate cages with hardwood bedding and maintained on AIN-76A semipurified diet under the following standard conditions: 20°±2° C., 50±10% relative humidity, 12 hours:12 hours light/dark cycle. Mice were randomized by weight into groups of 20–40 at an age of seven (7) weeks and administered corn oil or isothiocyanates (5 μmol/mouse/d.) by gavage once daily for four (4) consecutive days. Two (2) hours after the final dosing of each compound, a single dose of saline or NNK (10 μmol/mouse) was administered i.p. Sixteen (16) weeks after NNK administration, animals were sacrificed and pulmonary adenomas were quantitated.

The results of this experiment are shown in Table I. Based on body weights, these treatments did not appear to result in any overt toxicity. The corn oil-saline treatment combination yielded adenomas in 31% of the mice at a rate of 0.3 tumors/mouse. Groups treated with isothiocyanates prior only to saline administration generally developed tumor incidences similar to that of the corn oil-saline group. As expected, a single administration of NNK preceded by repetitve corn oil treatment resulted in a 100% incidence of pulmonary adenomas with a multiplicity of 9.2 tumors/mouse. Both PITC and BITC failed to affect the percentage of mice developing tumors or tumor multiplicity. However, PEITC pretreatment resulted in a 64% decrease in tumor multiplicity, but did not significantly reduce the percentage of mice that developed pulmonary adenomas (the relatively small dosages). PPITC and PBITC pretreatment resulted in remarkable inhibition of NNK-induced lung neoplasia, with percentages of tumor-bearing mice and tumor multiplicities much lower than those of PEITC pretreatment and similar to those of the corn oil-saline group. OPBITC, like PITC and BITC, provided no significant protection against NNK-induced lung neoplasia.

TABLE 1

Effects of isothiocyanates on NNK-induced pulmonary adenomas in A/J mice.[a]

| Treatment | No. of mice | Weight[b] | Tumors/mouse[b,c] | % of mice: with tumors |
|---|---|---|---|---|
| Corn oil + saline | 29 | 24.2 ± 0.6 | 0.3[1] ± 0.1 | 31% |
| PITC + saline + corn oil | 20 | 23.6 ± 0.7 | 0.2[1] ± 0.1 | 20% |
| BITC + saline + corn oil | 18 | 24.5 ± 0.6 | 0.4[1] ± 0.2 | 22% |
| PEITC + saline + corn oil | 20 | 24.0 ± 0.6 | 0.3[1] ± 0.1 | 25% |
| PPITC + saline + corn oil | 19 | 24.6 ± 0.6 | 0.4[1] ± 0.2 | 32% |
| PBITC + saline + corn oil | 19 | 23.9 ± 0.6 | 0.2[1] ± 0.1 | 16% |
| OPBITC + saline + corn oil | 18 | 23.7 ± 0.7 | 0.1[1] ± 0.1 | 6%* |
| Corn oil + NNK (in saline) | 39 | 21.9 ± 0.3 | 9.2[2] ± 0.5 | 100% |
| PITC + NNK (in saline) | 30 | 23.4 ± 0.4 | 9.8[2] ± 0.9 | 100% |
| BITC + NNK (in saline) | 29 | 22.1 ± 0.4 | 10.4[2] ± 0.7 | 100% |
| PEITC + NNK (in saline) | 28 | 22.4 ± 0.3 | 3.3[3] ± 0.4 | 93% |
| PPITC + NNK (in saline) | 30 | 22.0 ± 0.3 | 0.4[4] ± 0.1 | 37%* |
| PBITC + NNK (in saline) | 28 | 22.2 ± 0.5 | 0.4[4] ± 0.1 | 32%* |

TABLE 1-continued

Effects of isothiocyanates on NNK-induced pulmonary adenomas in A/J mice.[a]

| Treatment | No. of mice | Weight[b] | Tumors/mouse[b,c] | % of mice: with tumors |
|---|---|---|---|---|
| OPBITC + NNK (in saline) | 28 | 23.1 ± 0.4 | 7.9[2] ± 1.0 | 96% |

[a]Mice were administered corn oil or isothiocyanates (5 μmol/mouse/d) by gavage daily for four (4) consecutive days. Two (2) hours after the final dose of inhibitor, a single dose of NNK (10 μmol/mouse) was administered i.p. Sixteen (16) weeks after NNK administration, mice were sacrificed and pulmonary adenomas were quantitated.
[b]Mean ± SE
[c]Means in this column that bear different superscripts are significantly different from one another as determined by analysis of variance followed by Newman-Keuls' ranges test. Saline-treated groups and NNK-treated groups were tested separately.
*Significantly different from the appropriate control group as determined by the Chi-Square test.

In other studies, PEITC was found to inhibit NNK-induced lung neoplasia in A/J mice at four (4) consecutive daily doses of 5 or 25 μmol, whereas BITC and PITC, too toxic to be evaluated at a dose of 25 μmol, failed to inhibit NNK tumorigenesis at a daily dose of 5 μmol (Morse, M.A.; Amin, S.G.; Hecht, S.S.; and Chung, F-L. (1989), Effects of aromatic isothiocyanates on tumorigenicity, $O^6$-methylguanine formation, and metabolism of the tobacco-specific nitrosamine 4-(methylnitrosamino)-1-(3-pyridyl)-1-butanone in A/J mouse lung, Cancer Res., supra). PPITC and PBITC provided a remarkable inhibition of NNK-induced lung neoplasia compared to the other isothiocyanates. Hence, it appears that the inhibitory potentials of arylalkyl isothiocyanates toward NNK-induced lung neoplasia tend to increase as alkyl chain length increases.

Isothiocyanates have been shown to affect a number of different enzyme systems. Drobnica and Gemeiner demonstrated the complete inhibition of yeast alcohol dehydrogenase in vitro when incubated with BITC (Drobnica, L. and Gemeiner, P. (1976), Use of isothiocyanates as "reporter" groups in modification of enzymes, in Fox, J.L. et al. (eds.), Protein Structure and Evolution, Dekker, N.Y., pp. 105–115). Subchronic feeding of BITC at a concentration of 30 μmol/g. diet was found to induce glutathione-S-transferase activity in both the small intestine and liver of ICR/Ha mice (Sparnins, V.L., Venegas, P.L., and Wattenberg, L.W. (1982), Glutathione S-transferase activity: enhancement by compounds inhibiting chemical carcinogenesis and by dietary constituents, J. Natl. Cancer Inst., 68, 493–496). PEITC, BITC, and PITC were found to inhibit hepatic microsomal metabolism of N'-nitrosopyrrolidine and metabolism of N'-nitrosonornicotine by esophageal cultures when administered acutely to F344 rats (Chung, F-L., Juchatz, A., Vitarius, J., and Hecht, S.S. (1984), Effects of dietary compounds on α-hydroxylation of N-nitrosopyrrolidine and N'-nitrosonornicotine in rat target tissues, Cancer Res., 44, 2924–2928). In the same study, of these three isothiocyanates, only BITC failed to inhibit N-nitrosopyrrolidine metabolism by heptic microsomes and only PEITC failed to inhibit N'-nitrosonornicotine metabolism by esophageal cultures derived from rats fed isothiocyanates for two(2) weeks. PEITC, BITC, and PITC were also tested for their abilities to inhibit hepatic microsomal demethylation of NNK and N-nitrosodimethylamine. PEITC and PITC inhibited demethylation of either nitrosamine in hepatic microsomes prepared from rats administered these isothiocyanates acutely, whereas BITC had no effect. When fed subchronically for two(2) weeks, PEITC and PITC again inhibited nitrosamine demethylation in hepatic microsomes, while BITC actually induced demethylation of both (Chung. F-L., Wang, M., and Hecht, S.S. (1984), Effects of dietary indoles and isothiocyanates on N-nitrosodimethylamine and 4-(methylnitrosamino)-1-(3-pyridyl)-1-butanone α-hydroxylation and DNA methylation in rat liver, Carcinogenesis, 6, 539–543). Additionally, PEITC was shown to inhibit NNK metabolism in A/J lung microsomes prepared from animals given 5 or 25 μmol PEITC at two (2) hours prior to sacrifice (Morse, M.A.; Amin, S.G.; Hecht, S.S.; and Chung, F-L. (1989), Effects of aromatic isothiocyanates on tumorigenicity, $O^6$-methylguanine formation, and metabolism of the tobacco-specific nitrosamine 4-(methylnitrosamino)-1-(3-pyridyl)-1-butanone in A/J mouse lung, Cancer res., supra). The latter studies suggest that arylalkyl isothiocyanates possess a broad spectrum of inhibitory acitvities against nitrosamine metabolism.

PEITC has been shown to inhibit NNK-induced lung DNA methylation as well as NNK-induced lung neoplasia in F344 rats (Morse, M.A.; Wang, C-X.; Stoner, G.D; Mandal, S.; Conran, P.B.; Amin, S.G.; Hecht, S.S.; and Chung, F-L. (1989), Inhibition of 4-(methylnitrosamino)-1-(3-pyridyl)-1-butanone (NNK)-induced DNA adduct formation and tumorigenicity in lung of F344 rats by dietary phenethyl isothiocyanate, Cancer Res., 49, 549–553). PEITC decreased NNK-induced $O^6$-methylguanine formation in A/J mouse lung, while PITC and BITC had no significant effects (Morse, M.S.; Amin, S.G.; Hecht, S.S.; and Chung, F-L. (1989), Effects of aromatic isothiocyanates on tumorigenicity, $O^6$-methylguanine formation, and metabolism of the tobacco-specific nitrosamine 4-(methylnitrosamino)-1-(3-pyridyl)-1-butanone in A/J mouse lung, Cancer Res., supra). These studies show that inhibition of NNK-induced lung tumorigenesis is due to inhibition of DNA methylation, which is in turn caused by inhibition of enzymes responsible for NNK activation. Our results show that increasing alkyl chain length of arylalkyl isothiocyanates will yield increasing inhibition of both NNK-induced DNA methylation and NNK metabolism.

We have demonstrated the increased inhibitory activity of arylalkyl isothiocyanates towards NNK-induced lung neoplasia in A/J mice with increased alkyl chain length (from 2–4 carbons). We have also demonstrated the inhibitory effects of PPITC and PBITC.

Phenethyl isothiocyanate (PEITC) and benzyl isothiocyanate (BITC) are naturally occurring constituents of cruciferous vegetables, existing as their glucosinolate precursors, gluconasturtiin and glucotropaeolin, respectively (VanEtten, C. H.; Daxenbichler, M. E.; Williams, P. H.; and Kwolek, W. F. Glucosinolates and derived products in cruciferous vegetables. Analysis of the edible part from twenty-two varieties of cabbage. J. Agric. Food Chem. 24: 452–455,1976.; Carlson, D. G.; Daxenbichler, M. E.; VanEtten, C. H.; Tookey, M. L.; and Williams, P. H. Glucosinolates in crucifer vegetables;

turnips and rutabagas. *J. Agric. Food Chem.* 29: 1235–1239, 1981; Hanley, A. B.; Heaney, R. K.; and Fenwick, G. R. Improved isolation of glucobrassicin and other glucosinolates. *J.Sci. Food Agri.* 34: 869–873, 1983). The structures of PITC, BITC, PETIC, PPITC, PBITC, OPBITC, and NNK are shown below. These three isothiocyanates were found to inhibit mammary tumors induced by 7,12-dimethylbenz(α) anthracene (DMBA) in Sprague-Dawley rats when administered orally shortly prior to carcinogen administration; dietary PEITC and BITC were also found to inhibit DMBA-induced tumors of the forestomach and lung of ICF/Ha mice (Wattenberg, L. W. Inhibition of carcinogenic effects of polycyclic hydrocarbons by benzyl isothiocyanate and related compounds. *J. Natl. Cancer Inst.* 58: 395–398, 1978). Dietary BITC also proved effective in inhibiting DMBA-induced mammary tumors when administered following carcinogen exposure (Wattenberg, L. W. Inhibition of carcinogen-induced neoplasia by sodium cyanate, tert-buytl isocyanate, and benzyl isothiocyanate administered subsequent to carcinogen exposure. *Cancer Res.* 41: 2991–2994, 1981). Gulcotropaeolin was found to reduce both pulmonary neoplasia in A/J mice induced by benzo(α)pyrene (BP) and DMBA-induced mammary tumorigenesis in Sprague-Dawley rats (Wattenberg, L. W., Hanley, A. B., Barany, G., Sparnins, V. L., Lam, L. K. T., and Fenwick, G. R. Inhibition of carcinogenesis by some minor dietary constituents. In Hayashi, Y., Nagao, M., Sugimura, T., Takayama, S., Tomatis, L., Wattenberg, L. W., and Wogan, G. N. (eds), *Diet, Nutrition and Cancer.* Japan Sci. Soc. Press, London/VNU Sci. Press Utrecht, pp. 193–203, 1986). BITC administered shortly before carcinogen treatment was found to inhibit N-nitrosodiethylamine-induced forestomach tumors and BP-induced lung and forestomach tumors in A/J mice (Wattenberg, L. W. Inhibitory effects of benzyl isothiocyanate administered shortly before diethylnitrosamine or benzo (α) pyrene on pulmonary and forestomach neoplasia in A/J mice. *Carcinogenesis* 8: 1971–1973, 1987.)

4-(Methylnitrosamino)-1-(3-pyridyl)-1-butanone (NNK) is the most potent tobacco-specific carcinogenic nitrosamine known (Hoffmann, D., and Hecht, S. S. Smokeless tobacco and cancer. *ISI Atlas of Science: Pharmacology,* 46–52, 1988). NNK induces lung tumors in all species tested, regardless of the route of administration used (International Agency for Research on Cancer. Evaluation of the carcinogenic risk of chemicals to humans: tobacco habits other than smoking; betel quid and areca nut chewing; and some related nitrosamines. *IARC Monographs* 37: 209–224, 1985). These facts suggest a possible role for NNK in the induction of lung cancer in smokers. Recently, we have examined the inhibitory effects of dietary PEITC on NNK-induced tumorigenesis and NNK-induced DNA adduct formation in F344 rats (Morse, M. A., Wang, C. X., Stoner, G. D., Mandal, S., Conran, P. B., Amin, S. G., Hecht, S. S., and Chung, F.-L. Inhibition of 4-(methylnitrosamino)-1-(3-pyridyl)-1-butanone (NNK)-induced DNA adduct formation and tumorigenicity in lung of F344 rats by dietary phenethyl isothiocyanate. *Cancer Res.* 49: 549–553, 1989). The results indicated that the inhibitory effect of PEITC on NNK-induced lung tumorigenesis could be attributed to its ability to inhibit NNK-induced DNA methylation in rat lung. In the present study, in order to develop a more rapid means of screening inhibitors of NNK tumorigenicity and to verify the importance of DNA adduct formation in NNK tumorigenesis, we have examined the effects of PEITC, BITC, and PITC on NNK-induced pulmonary adenoma formation and NNK-induced $O^6$-methylguanine ($O^6$-mGua) formation in A/J mice. Additionally, we have investigated the effect of PEITC pretreatment on A/J mouse lung microsomal metabolism of NNK.

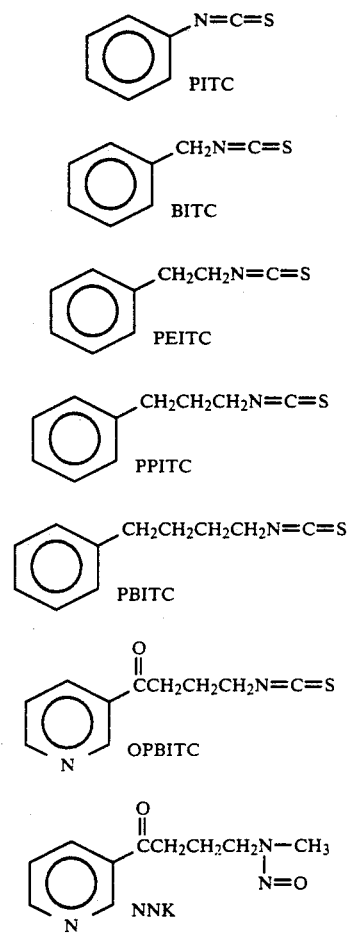

MATERIALS AND METHODS

Animals

Female A/J mice of 5–6 wks of age were obtained from Jackson Laboratories (Bar Harbor, ME) and used in experiments at 6–7 wks. of age. Mice were grouped 10 per cage in polycarbonate cages with hardwood bedding and were maintained at the following standard conditions: 20°±2° C., 50±10% relative humidity, 12 hours: 12 hours light/dark cycle.

Chemicals

Unlabelled NNK and NNK metabolite standards were synthesized as known (McKennis, H., Jr., Schwartz, S. L., Turnbull, L. B., Tamaki, E., and Bowman, E. R. The metabolic formation of gamma-(3-pyridyl)-gamma-hydroxybutyric acid and its possible intermediary role in the mammalian metabolism of nicotine. *J. Biol. Chem.* 239: 3981–3989, 1964; Hecht, S. S., Young, R., and Chen, C. B. Metabolism in the F344 rat of 4-(N-methyl-N-nitrosamino)-1-(3-pyridyl)-1-butanone, a tobacco-specific carcinogen. *Cancer Res.* 40:

4144–4150, 1980; Hecht, S. S., Lin, D., and Castonguay, A. Effects of alpha-deuterium substitution on the mutagenecity of 4-(methylnitrosamino)-1-(3-pyridyl)-1-butanone (NNK). *Carcinogenesis* 4: 305–310, 1983). [5-$^3$H]NNK(1.3 Ci/mmol) and O$^6$-mGua were purchased from Chemsyn Science Laboratories (Lenexa, KS). PEITC, BITC, and PITC were purchased from Aldrich Chemical Company (Milwaukee, WI). When analyzed by reversed phase HPLC, these isothiocyanates were found to have a purity of at least 99%. Glucose-6-phosphate, glucose-6-phosphate dehydrogenase, magnesium chloride, EDTA, NADP+, and ammonium sulfate were obtained from Sigma Chemical Company (St. Louis, MO). BCA (bicinchoninic acid) protein assay reagents were obtained from Pierce Chemical Co. (Rockford, IL).

A/J MOUSE PULMONARY ADENOMA PROTOCOL

Groups of 20-30 female A/J mice were administered PEITC (5 or 25 μmol/day), BITC (5 μmol/day), PITC (5 μmol/day), or corn oil vehicle by gavage for four consecutive days. (Both BITC and PITC proved too toxic to test at a dose of 25 μmol/day.) On the fourth day, NNK was administered i.p. at a dose of 10 μmol/mouse 2 hours after the final gavaging of isothiocyanates. All animals were maintained on AIN-76A diet for the first 10 days of the experiment and then placed on NIH-07 diet. Sixteen wks. after NNK dosing, mice were sacrificed and pulmonary adenomas were counted. Statistical comparison of tumor multiplicities among the various groups was performed by analysis of variance followed by Newman-Keuls' ranges test. Comparisons of the proportions of animals in groups that developed tumors was performed by the Chi-Square test.

DETERMINATION OF O$^6$-MGUA LEVELS IN A/J MOUSE LUNG

Groups of 10 mice were administered isothiocyanates (5 or 25 μmol/day) or corn oil by gavage for four consecutive days. On the fourth day, NNK (10 μmol/mouse) was administered 2 hours after the final gavage. Groups of 5 animals were sacrificed by cervical dislocation at 2 and at 6 hours following NNK dosing and the lungs of each animal were excised and stored at −20° C. DNA was isolated from the individual lungs of animals by a modification of the method of MarMur (Marmur, J. A procedure for the isolation of deoxyibonucleic acid from microorganisms. *J. Mol. Biol.* 3: 208–218, 1961) and purified by the method of Sebti et al. (Sebti, S. M., Pruess-Schwartz, D. M., and Baird, W. M. Species and length of exposure-dependent differences in the benzo(a)pyrene: DNA adducts formed in embryo cell cultures from mice, rats, and hamsters. *Cancer Res.* 42: 1594–1600, 1985). This method of DNA purification has been shown to yield DNA that is virtually free of RNA contamination. Purified DNA samples were hydrolyzed in 0.1N HCL for 60 min at 80° C. Pre-HPLC sample purification was accomplished by the use of Gelman Acrodiscs (Ann Arbor, MI). Guanine and O$^6$-mGua were separated and quantitated by strong cation exchange HPLC and fluorescence detection as described previously (Castonguay, A.; Lin, D.; Stoner, G. D.; Radok, P.; Furuya, K.; Hecht, S. S.; Schut, H. A. J.; and Klaunig, J. E. Comparative carcinogenicity in A/J mice and metabolism by cultured mouse peripheral lung of N'-nitrosonornicotine, 4-(methyl-nitrosamino)-1-(3-pyridyl)-1-butanone, and their analogues. *Cancer Res.* 43: 1223–1229, 1983) except that the buffer used in isocratic elution of these compounds was 0.1M ammonium phosphate (pH=2.0) in 5% methanol. The identities of guanine and O$^6$-mGua were confirmed by coelution with authentic standards. NNK Metabolism in A/J Lung Microsomes Groups of 4 female A/J mice were administered a single dose of PEITC (5 or 25 μmol) or corn oil 2 hours prior to sacrifice. Excised lungs were homogenized in 1.15% KCl-0.05M sodium phosphate, pH-7.4 and centrifuged at 9000 gs for 30 min at 5° C. The supernatants were removed and further centrifuged at 105,000 gs for 60 min at 5° C. The supernatants were discarded and the pellets were resuspended in buffer and recentrifuged at 105,000 g for another 60 min. The microsomal pellets were then suspended in 0.25M sucrose and stored frozen until used. Protein was quantitated by use of the Pierce BCA protein assay.

Samples constituting 200 μg of microsomal protein were incubated in 0.8 ml of solution at 37° C. for 60 min. The concentrations of the various solution components were as follows: 100 mM sodium phosphate (ph=7.4), 3.0 mM MgCl$_2$, 1.0 mM EDTA, 1.0 mM NADP+, 5.0 mM glucose-6-phosphate, 3.8 units/ml glucose-6-phosphate dehydrogenase, and 10.0 μM NNK(1.0 μCi of 5-$^3$H]NNK). Following incubation, 0.2 ml of saturated ammonium sulfate was added to each vial to precipitate protein. Samples were freed of protein prior to HPLC analysis by the use of Amicon Centrifree tubes (Amicon Corp., Danvers, MA). Separation and quantitation of NNK metabolites was performed by reversed-phase HPLC. The HPLC system used consisted of a model 7125 Rheodyne injection valve, a Waters automated gradient controller, two Waters 510 pumps, a Knauer uv detector, and a Beta Flo-One radioflow detector. An Alltech Versapack C$_{18}$ column (4.1 mm i.d.×300 mm length) was eluted with a linear gradient of 100% of buffer A (0.02M sodium phosphate, pH=7.4) to 65% buffer A:35% methanol over a 70 min period. The identities of the metabolites were established by coelution with authentic uv standards.

TABLE 2

| | Effects of isothiocyanates on NNK-induced pulmonary adenomas in A/J mice | | | | |
|---|---|---|---|---|---|
| Pretreatment | Daily Dose (μmol) | N | Weight at Sacrifice (g) | % of Mice with Tumors | Tumors/Mouse |
| 1. None | — | 30 | 23.8 | 100 | 10.7$^1$ ± 0.8 |
| 2. PEITC | 5 | 18 | 23.0 | 89 | 2.6$^2$ ± 0.4 |
| 3. PEITC | 25 | 20 | 24.2 | 30$^c$ | 0.3$^3$ ± 0.1 |
| 4. BITC | 5 | 20 | 24.4 | 100 | 7.6$^1$ ± 0.5 |
| 5. PITC | 5 | 20 | 23.5 | 100 | 9.5$^1$ ± 1.2 |

$^a$Groups of 20-30 A/J mice were administered corn oil or isothiocyanates by gavage daily for four consecutive days. Two h after the final gavaging, a single dose of NNK (10 μmol/mouse) was administered i.p. Sixteen weeks after NNK administration, mice were sacrific- i and pulmonary adenomas were quantitated.
$^b$Mean ± SE. Means bearing different superscripts under the tumors/mouse heading are statistically different (p < 0.05) from one another as determined by analysis of variance followed by Newman-Keuls' ranges test.
$^c$Significantly (p < 0.01) less than that of group 1 as determined by the Chi-Square test.

RESULTS

Pulmonary Adenoma Assays

As shown in Table 2, a single i.p. administration of NNK at a dose of 10 μmol/mouse resulted in a 100% incidence of pulmonary adenomas with an accompanying multiplicity of 10.7 tumors/mouse. The 5 μmol daily dose (20 μmol total) of PEITC did not significantly reduce the proportion of mice that developed pulmonary adenomas, but resulted in an approximate 70% reduction in tumor multiplicity. The 25 μmol daily dose (100 μmol total) of PEITC resulted in a 70% reduction of the percentage of mice that developed tumors and a nearly complete inhibition of tumor multiplicity. However, pretreatment with BITC for 4 days at 5 μmol/day resulted in no change in the percentage of mice that developed tumors and caused only a 29% reduction in tumor multiplicity, which by the multiple-comparison statistics utilized, was not significantly different from the control tumor multiplicity. Similarly, PITC administration at 5 μmol/day had no significant effects on the percentage of mice with tumors or on tumor multiplicity.

It should be noted that both BITC and PITC proved too toxic to be tested at a dose of 25 μmol for four consecutive daily administrations. At this dose, we found that PITC resulted in 100% mortality after two administrations. No apparent toxicity occurred upon administration of BITC or PITC at a daily dose of 5 μmol. Also, neither the 5 μmol dose nor the 25 μmol dose of PEITC resulted in any overt toxicity. Thus, besides being a better inhibitor of NNK tumorigenesis in A/J mice than either BITC or PITC, PEITC appears to be considerably less toxic.

TABLE 3

Effects of isothiocyanates on NNK-induced $O^6$-methylguanine formation in A/J mouse lung.[a]

| Pretreatment | Daily Dose (μmol) | μmol $O^6$-mGua/mol guanine[b] 2 h | 6 h |
|---|---|---|---|
| 1. None | — | $33.1^1 \pm 1.4$ | $30.9^1 \pm 5.9$ |
| 2. PEITC | 5 | $10.6^2 \pm 4.9$ | $3.9^2 \pm 1.2$ |
| 3. PEITC | 25 | $12.8^2 \pm 5.2$ | N.D.[c] |
| 4. BITC | 5 | $36.0^1 \pm 6.0$ | $26.1^1 \pm 6.7$ |
| 5. PITC | 5 | $42.1^1 \pm 3.8$ | $29.7^1 \pm 4.4$ |

[a]Groups of 5 mice were administered corn oil or isothiocyanates by gavage for four consecutive days. Two h after the final gavaging, NNK was administered i.p. at a dose of 10 μmol/mouse. Mice were sacrificed at 2 or at 6 h after NNK administration. Isolation of DNA and quantitation of guanine and $O^6$-mGua were performed as described in "Materials and Methods".
[b]Mean ± SE of 4-5 mice. Means that bear different superscripts within a given column are statistically different (p < 0.05) from one another as determined by analysis of variance followed by Newman-Keuls' ranges test.
[c]Not detected

$O^6$-mGua Assays

In an effort to relate the effects of PEITC, BITC, and PITC on NNK lung tumorigencicity to in vivo NNK:DNA adduct formation, the effects of these isothiocyanates on NNK-induced $O^6$-mGua in A/J lung DNA were investigated. The same dosing regimen employed in the pulmonary adenoma assays was used in the $O^6$-mGua assays. As shown in Table 3, at 2 hours after NNK administration, both doses of PEITC resulted in an approximate two-thirds reduction of $O^6$-mGua when compared to that of controls. However, neither BITC nor PITC had any significant effect on $O^6$-mGua levels at 2 hours. At 6 hours after NNK administration, the 5 μmol daily dose of PEITC resulted in an 87% reduction of $O^6$-mGua levels while the 25 μmol daily dose of PEITC yielded $O^6$-mGua levels that were undetectable. (Given lung DNA yields of 350-500 μg/mouse, the limit of detection in our system is approximately 1.0 μmol $O^6$-mGua/mol guanine.) At 6 hours, BITC and PITC pretreatment again resulted in no significant reduction in $O^6$-mGua levels. On the whole, the effects of the isothiocyanates on NNK-induced $O^6$-mGua formation were in good agreement with their effects on NNK lung tumorigenicity.

TABLE 4

Effect of PEITC pretreatment on A/J mouse lung microsomal metabolism of NNK.[a]

| Pretreatment | pmol product/min/mg microsomal protein[b] keto alcohol | NNAL | percentage of NNK metabolized[b] |
|---|---|---|---|
| 1. None | $19.2^1 \pm 2.3$ | $99.7^1 \pm 9.1$ | $19^1 \pm 1$ |
| 2. 5 μmol PEITC | $4.1^2 \pm 0.7$ | $9.9^2 \pm 1.3$ | $1.5^2 \pm 0.1$ |
| 3. 25 μmol PEITC | $3.6^2 \pm 0.5$ | $10.7^2 \pm 1.7$ | $1.5^2 \pm 0.3$ |

[a]Groups of 4 mice were pretreated with corn oil, 5 μmol PEITC, or 25 μmol PEITC and sacrificed 2 h later. Microsomes were immediately prepared from the liver and lungs of each mouse. Isolation of microsomes, incubations of NNK in microsomal preparations, and quantitation of metabolites by reversed phase HPLC are described in "Materials and Methods".
[b]Mean ± SE of the determinations from four preparations. Values in the same column that bear different superscripts are statistically different (p < 0.05) from each other as determined by analysis of variance followed by Newman-Keuls' ranges test.

NNK MICROSOMAL METABOLISM ASSAYS

Based on its ability to inhibit effectively both NNK-induced tumorigenicity and $O^6$-mGua formation, PEITC was further tested for its ability to inhibit the microsomal metabolism of NNK. Table 4 shows the effects on lung microsomal NNK metabolism of pretreatment with single doses of 5 or 25 μmol PEITC, 2 hours prior to sacrifice. Microsomes from untreated mice yielded four possible metabolites of NNK; two were identified as NNAL [4-(methylnitrosamino)-1-(3-pyridyl)-1-butanol] and keto alcohol [4-hydroxy-1-(3-pyridyl)-1-butanone], respectively, while two early eluting peaks could not be precisely identified on the basis of coelution with uv standards. Keto alcohol is formed as a result of α-hydroxylation of NNK. The N-oxides of NNK and NNAL were not detected. All of these identified metabolites were previously found to be formed by cultured A/J mouse lung (Castonguay, A., Lin, D., Stoner, G. D., Radok, P., Furuya, K., Hecht, S. S., Schut, H. A. J., and Klaunig, J. E. Comparative carcinogenicity in A/J mice and metabolism by cultured mouse peripheral lung of N'-nitrosonornicotine, 4-(methyl-nitrosamino)-1-(3-pyridyl)-1-butanone, and their analogues. Cancer Res. 43: 1223-1229, 1983).

Under the assay conditions, the limit of detection of each metabolite was approximately 0.5 pmol/min/mg protein. In all microsomal incubations, NNAL was the major metabolite produced. Both the 5 μmol and the 25 μmol daily doses of PEITC decreased keto alcohol formation by approximately 80% and NNAL production by roughly 90%. The total percentage of NNK metabolism was also decreased by approximately 90% by pretreatment with either dose of PEITC. Such an inhibition of NNK metabolism readily accounted for the reduction of NNK-induced $O^6$-mGua formation in vivo by PEITC.

In the pulmonary adenoma assay protocol utilized, a single i.p. dose of 10 μmol NNK induced a readily detectable lung tumor response (100% incidence in controls, with 10.7 tumors/mouse) in just sixteen wks. In previous work, NNK (total dose 110 μmol) was administered to A/J mice over a 7.3 wk period followed by a 30 wk period prior to sacrifice. This treatment resulted in tumor formation in 100% of the mice, with a multiplicity of 19.7 tumors/mouse (Castonguay, A., Lin, D., Stoner, G. D., Radok, P., Furuya, K., Hecht, S. S., Schut, H. A. J., and Klaunig, J. E. Comparative carcinogenicity in A/J mice and metabolism by cultured mouse peripheral lung of N'-nitrosonornicotine, 4-(methyl-nitrosamino)-1-(3-pyridyl)-1-butanone, and their analogues. *Cancer Res.* 43: 1223-1229, 1983). Repetitive administration of NNK (three times weekly for 20 wk) to F344 rats at total doses of 0.3 and 0.5 mmol/kg resulted in lung tumor formation in 75% and 80% of rats two years after initiation of the dosing regimen (Morse, M. A., Wang, C.-X., Stoner, G. D., Mandal, S., Conran, P. B., Amin, S. G., Hecht, S. S., and Chung, F.-L. Inhibition of 4-(methylnitrosamino)-1-(3-pyridyl)-1-butanone (NNK)-induced DNA adduct formation and tumorigenicity in lung of F344 rats by dietary phenethyl isothiocyanate. *Cancer Res.* 49: 549-553, 1989; Hecht, S. S., Trushin, N., Castonguay, A. and Rivenson, A. Comparative tumorigenicity and DNA methylation in F344 rats by 4-(methylnitrosamino-1-(3-tumorigenicity and DNA methylation in F344 rats by 4-(methylnitrosamino)-1-(3-pyridyl)-1-butanone and N-nitrosodimethylamine. *Cancer Res.* 46: 498-502, 1986). Thus, the current protocol provides a simple, rapid means of testing potential inhibitors of NNK tumorigenicity.

Previous studies have demonstrated that certain inhibitors of tumorigenesis yield a similar inhibition in DNA adduct formation. Anderson et al. (Anderson, M. W., Goroujerdi, M., and Wilson, A. G. E. Inhibition in vivo of the formation of adducts between metabolies of benzo(a)pyrene and DNA by butylated hydroxyanisole. Cancer Res. 41: 4309-4315, 1981) showed that butylated hydroxyanisole, a potent inhibitor of BP-induced lung neoplasia in A/J mice, decreased BP:DNA adduct formation in A/J mouse lung. Bull et al. (Bull, A. W., Burd, A. D., and Nigro, N. D. Effect of inhibitors of tumorigenesis on the formation of $O^6$-methylguanine in the colon of 1,2-dimethylhydrazine-treated rats. *Cancer Res.* 41: 4938-4941, 1981) demonstrated that both disulfiram and pyrazole, inhibitors of 1,2-dimethylhydrazine-induced colon tumorigenesis (Wattenberg, L. W. Inhibition of dimethylhydrazine-induced neoplasia of the large intestine by disulfiram. *J. Natl. Cancer Inst.* 54: 1005-1006, 1975), decreased $O^6$-mGua formation in the colon of 1,2-dimethylhydrazine-treated rats. Our results are consistent with these findings, since PEITC inhibited both tumorigenicity and $O^6$-mGua formation induced by NNK in mouse lung. Metabolic α-hydroxylation of NNK results in both methylation and pyridyloxobutylation of DNA (Hecht, S. S., Spratt, T. E., and Trushin, N. Evidence for 4-(3-puridyl)-4-oxobutylation of DNA in F344 rats treated with the tobacco-specific nitrosamines 4-(methylnitrosamino)-1-(3-pyridyl)-1-butanone and N'-nitrosonornicotine. *Carcinogenesis* 9:161-165, 1988).

Recent work by Belinsky and colleagues has indicated the importance of the promutagenic adduct $O^6$-mGua in NNK tumorigenesis of F344 rat lung. $O^6$-mGua was found to be much more persistent than either 7-methylguanine or $O^4$-methylthymidine (Belinsky, S. A., White, C. M., Boucheron, J. A., Richardson, F. C., Swenberg, J. A., and Anderson, M. W. Accumulation and persistence of DNA adducts in respiratory tissues of rats following multiple administrations of the tobacco-specific carcinogen 4-(N-methyl-N-nitrosamino)-1-(3-pyridyl)-1-butanone. *Cancer Res.* 46: 1280-1284, 1986). Additionally, $O^6$-mGua was found to be most highly accumulated in Clara cells (Belinsky, S. A., White, C. M., Devereux, T. R., Swenberg, J. A., and Anderson, M. W. Cell selective alkylation of DNA in rat lung following low dose exposure to the tobacco specific carcinogen 4-(N-methyl-N-nitrosamino)-1-(3-pyridyl)-1-butanone. *Cancer Res.* 47: 1143-1148, 1987), the presumed progenitor cells of NNK rat lung neoplasia (Kauffman, S. L. Histogenesis of the papillary Clara cell adenoma. *Am. J. Pathol.* 103: 174-180, 1981; Reznik-Schuller, H., and Hague, B. F, A morphometric study of the pulmonary Clara cell in normal and nitrosoheptamethyleneimine-treated European hamsters. *Exp. Pathol. (Jena)* 18: 366-371, 1980). The parallel effects of PEITC, BITC, and PITC on NNK mouse lung tumorigenesis and $O^6$-mGua formation lend further credence to the importance of this adduct in NNK tumorigenesis.

Our work serves as a basis for the elucidation of structure-activity relationships of isothiocyanates toward inhibition of NNK tumorigenesis. The two-carbon alkyl chain homolog PEITC was clearly more potent in reducing NNK tumorigenicity and $O^6$-mGua formation than either BITC or PITC. The toxicities of these isothiocyanates appear to be inversely related to alkyl chain length. PEITC, the least toxic of these three isothiocyanates, had no apparent toxic effects at the 25 μmol daily dose level while both BITC and PITC proved too toxic to test at this dose.

A number of studies have shown that the relative potencies of these three isothiocyanates in inhibition of a tumorigenesis or of tumorigenic parameters could vary. In previous experiments conducted by Wattenberg, (Wattenberg, L. W. Inhibition of carcinogenic effects of polycyclic hydrocarbons by benzyl isothiocyanate and related compounds. *J. Natl. Cancer Inst.* 58: 395-398 1987), both BITC and PITC inhibited DMBA-induced mammary tumors in Sprague-Dawley rats as effectively if not more effectively than PEITC. In the same study, dietary BITC and PEITC appeared to inhibit DMBA-induced pulmonary adenomas equally well in ICR/Ha mice. In our previous work (Chung, F. -L., Wang, M., and Hecht, S. S. Effects of dietary indoles and isothiocyanates on N-nitrosodimethylamine and 4-(methylnitrosamino)-1-(3-pyridyl)-1-butanone alpha-hydroxylation and DNA methylation in rat liver. *Carcinogenesis* 6: 539-543, 1985), PEITC and PITC inhibited NNK demethylation in F344 rat liver microsomes when administered acutely via gavage or chronically in the diet. Additionally, both compounds inhibited NNK-induced in vivo methylation of hepatic DNA when administered acutely or chronically to rats. In the same study, BITC had no effect on NNK hepatic microsomal metabolism when administered acutely, and actually induced NNK demethylation after chronic administration. Ultimately, the doses of isothiocyanates used, the time of their application in relationship to carcinogen administration, their availability to a given target tissue, and the precise nature of their effects on enzymes of carcinogen activation may play substantial roles in determining their inhibitory activities in a given system.

This inhibitory activity of PEITC can readily be explained by its inhibition of NNK metabolism. While no dose-response relationship was evident in the inhibition of NNK metabolism by PEITC, such an effect could be manifested by a more long-lived effect at the higher dose of PEITC; such a phenomenon could only be detected by the examination of microsomes prepared from mice sacrificed at several different time points following PEITC administration.

In summary, we have shown that PEITC effectively inhibits NNK tumorigenicity and NNK-induced $O^6$- mGua formation in the lungs of A/J mice, while BITC and PITC have virtually no effect on either parameter. The inhibitory activity of PEITC appears to be related to its inhibitory effects on NNK metabolism in A/J mouse lung microsomes. These results, when combined with our results in F344 rats (Morse, M. A., Wang, C.-X, Stoner, G. D., Mandal, S., Conran, P. B., Amin, S. G., Hecht, S. S., and Chung, F.-L. Inhibition of 4-(methylnitrosamino)-1-(3-phenethyl) isothiocyanate. Cancer Res. 49: 549-553, 1989) firmly establish PEITC as an effective inhibitor of NNK lung tumorigenesis in rodents.

In accordance with the aforenoted trend of increased inhibitory activity of arylalkyl isothiocyanates toward NNK-induced lung neoplasia in A/J mice with increased alkyl chain length, we synthesized and evaluated phenylpentyl isothiocyanate ("PPeITC") and phenylheyl isothiocyanate ("PHITC") for such inhibitory activity.

Phenylalkyl chloride (n=5 or 6) (10 g, 51 mmol) (see scheme at Table 5) was dissolved in 300 ml DMF. Sodium azide ($NaN_3$) was added (5 g, 77 mmol). The mixture was heated for 3 hr at 80° C. while stirring. Solvent was evaporated, the residue dissolved in $CH_2Cl_2$, washed with water then purified on a short silica gel column using solvent system (hexane:toluene 10:1) yielding 9.3 g (85%) of the azide 1*($R_f$=0.6).

* These numerals represent the structures indicated by the corresponding numerals in Table 5

1*(9 g, 44.3 mmol) was dissolved in 500 ml isopropanol and heated at refluxing temperature while 5 g $NaBH_4$ was carefully added. The mixture was refluxed for 3 days and additional 2.5 g $NaBH_4$ was carefully added. After refluxing for a total of 7 days, the solvent was evaporated. The residue was dissolved in $CHCl_3$ and washed with water. $CHCl_3$ layer was dried with $MgSO_4$, filtered and evaporated yielding 8 g of 2* which was used directly in the next step.

* These numerals represent the structures indicated by the corresponding numerals in Table 5

Eight g of crude 2* was evaporated 3 times with 1M HCl to convert the amine to ammonium chloride. The hydrochloride was dissolved in 200 ml of $H_2O$ and stirred, then thiophosgene 10.3 g (6.8 ml, 90 mmol) dissolved in 200 ml $CHCl_3$ with a small amount of phenolphthaleine was added with stirring. NaOH (1M) was added carefully at room temperature at such a rate that the aqueous phase remained alkaline. Then the reaction mixture was stirred at room temperature for an additional hour. The $CHCl_3$-phase was washed several times with $H_2O$, dried with $MgSO_4$, filtered and evaporated to give 6.5 g of the final product after purification on a silica gel column (hexane:toluene 10:1).

* These numerals represent the structures indicated by the corresponding numerals in Table 5

TABLE 5

Synthesis of Phenylpentyl isothiocyanate and Phenylhexyl isothiocyanate

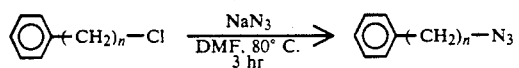

n = 5 and 6   1 yield: ~85%

TABLE 5-continued

Synthesis of Phenylpentyl isothiocyanate and Phenylhexyl isothiocyanate

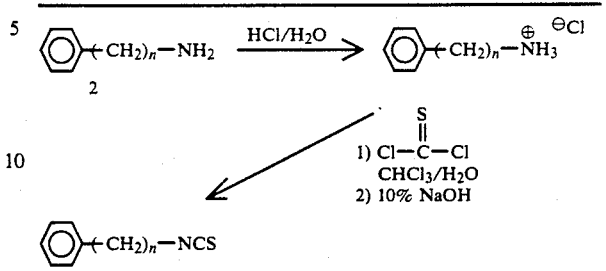

n = 5 and 6
for n = 5 yield = 70%:
from —$N_3$ to —NCS

NMR ($^1$H and $^{13}$C) and mass spectra (EI) verifies the structures
DMF represents N,N-dimethylformamide We then devised an experiment to study the effects of these arylalkyl isothiocyanates (PPeITC and PHITC) on NNK-induced lung tumorigenicity in A/J mice. Groups of 20 A/J mice (controls: 60 mice) were administered corn oil vehicle or isothiocyanates (in 0.1 ml corn oil) by gavage for 4 consecutive days. At 2 h after the final pretreatment, mice were administered 10 μmol NNK (in 0.1 ml saline) i.p. 16 weeks after NNK administration, mice were killed and pulmonary adenomas were quantitated. The results are shown in Table 6.

TABLE 6

| Treatment | Dose (μmol) | tumor multiplicity | (number of tumors per mouse) | tumor incidence |
|---|---|---|---|---|
| corn oil/NNK | | 7.9 ± 0.4[1] | | 100%[1] |
| PEITC | 5 | 4.1 ± 0.8[2] | | 93%[1,2,3] |
| | 1 | 6.5 ± 1.4[1] | | 100%[2,3,4] |
| | 0.2 | 9.9 ± 0.8[3] | | 100%[1,2] |
| PPITC | 5 | 0.2 ± 0.1[4] | | 11%[5,6] |
| | 1 | 1.2 ± 0.3[4] | | 75%[2,3,4] |
| | 0.2 | 3.7 ± 0.6[2] | | 90%[1,2,3] |
| PBITC | 5 | 0.2 ± 0.1[4] | | 11%[5,6] |
| | 1 | 0.8 ± 0.3[4] | | 42%[3,4,5,6] |
| | 0.2 | 4.2 ± 0.6[2] | | 100%[1,2] |
| PPeITC | 5 | 0.3 ± 0.1[4] | | 25%[4,5,6] |
| | 1 | 0.9 ± 0.3[4] | | 53%[2,3,4,5] |
| | 0.2 | 3.0 ± 0.4[2] | | 100%[1,2] |
| PHITC | 5 | 0.1 ± 0.1[4] | | 5%[5,6] |
| | 1 | 0.0 ± 0.0[4] | | 0%[6] |
| | 0.2 | 1.2 ± 0.3[4] | | 70%[2,3,4] | multiplicity = No. of tumors/mouse
Means that bear different superscripts within a given column are statistically different ($p < 0.05$) from one another as determined by analysis of variance followed by Newman-Keuls' ranges test.

The results in Table 6 show that the inhibitory effects of PPeITC and PHITC are even more remarkable than the inhibitory effects of PPITC and PBITC. Moreover, our studies have shown that the lowest total dose of PHITC tested which inhibited NNK lung tumors by 85% in A/J mice was about 0.2 mg, one tenth of the dose of NNK administered (2.0 mg). For comparison purposes, average smokers are exposed to about 1 mg of NNK per year. Extrapolating the results of our studies to humans, only about 0.1 mg per year of PHITC would be needed for the protection of NNK-caused lung cancer. It may therefore be appreciated that compounds of the instant invention could be effective in reducing NNK-induced lung tumors in humans in the mg/year range.

The results of Table 6 confirm that arylalkyl isothiocyanates with increased alkyl-chain length have increased inhibitory activity toward NNK-induced tumorigenesis. We hypothesize that arylalkyl isothiocyanates with longer alkyl chains have higher lipid solubility and a higher degree of bulkiness and that these two factors could be determinants of potency of the subject inhibitors. We expect a limit where further increase in the alkyl chain length would result in a decreased inhibitory effect and another limit where still further increase in the alkyl-chain length would render the resultant arylalkyl isothiocyanates ineffective as inhibitors of NNK-induced tumorigenesis.

The arylalkyl isothiocyanates of the instant invention may be administered as a dietary supplement. For example, they may be administered orally, Alternatively, and not by way of limitation, we foresee that they may be blended into cigarettes for inhalation along with the carcinogens they are intended to inhibit.

There will now be obvious to those skilled in the art many modifications and variations of the methods and compounds which have been described hereinabove. These modifications and variations will not depart from the scope of the invention if defined by the following claims.

What is claimed is:

1. Phenylhexyl isothiocyanate.

* * * * *